(12) United States Patent
Itoi (10) Patent No.: US 6,673,021 B2
(45) Date of Patent: Jan. 6, 2004

(54) ULTRASOUND PROBE FOR ULTRASOUND EXAMINATION SYSTEM

(75) Inventor: Hiromu Itoi, Yoshikawa (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 10/256,012

(22) Filed: Sep. 27, 2002

(65) Prior Publication Data

US 2003/0065261 A1 Apr. 3, 2003

(30) Foreign Application Priority Data

Sep. 28, 2001 (JP) ........................................ 2001-302031

(51) Int. Cl.[7] ................................................ A61B 8/14
(52) U.S. Cl. ...................... 600/466; 600/437; 600/459; 604/510; 604/528
(58) Field of Search ................................ 600/437–472, 600/104–110, 127–150, 585

(56) References Cited

U.S. PATENT DOCUMENTS

| | | | | |
|---|---|---|---|---|
| 4,426,886 A | * | 1/1984 | Finsterwald et al. ............ 73/633 |
| 4,991,588 A | * | 2/1991 | Pflueger et al. ............. 600/467 |
| 5,150,715 A | * | 9/1992 | Ishiguro et al. ............. 600/463 |
| 5,176,142 A | * | 1/1993 | Mason ....................... 600/463 |
| 5,320,104 A | * | 6/1994 | Fearnside et al. ........... 600/463 |
| 5,368,035 A | * | 11/1994 | Hamm et al. ............... 600/463 |
| 5,372,138 A | * | 12/1994 | Crowley et al. ............. 600/463 |
| 5,596,991 A | * | 1/1997 | Tanaka ..................... 600/459 |
| 5,827,175 A | * | 10/1998 | Tanaka ..................... 600/104 |
| 5,967,988 A | * | 10/1999 | Briscoe et al. ............. 600/458 |

* cited by examiner

Primary Examiner—Dennis Ruhl
Assistant Examiner—William C. Jung
(74) Attorney, Agent, or Firm—Oblon, Spivak, McClelland, Maier & Neustadt, P.C.

(57) ABSTRACT

Attached to a proximal end portion of a flexible cord of an ultrasound probe of an ultrasound examination system, to be introduced into a body cavity through a narrow guide passage, is a flexible wiring film which can be coiled into a helical roll of a narrow cylindrical shape extending along an axial extension line of the flexible cord at the time of passing same through the narrow guide passage. Formed on a surface of the flexible wiring film are a plural number of wire connection points for connection of signal lines from transducer elements of an ultrasound transducer which is provided at a fore distal end of the flexible cord of the probe, and a corresponding number of electrodes which are electrically connected with the wire connection points through a wiring pattern. The electrodes on the flexible wiring film are disconnectibly connected to corresponding contact points on a contact assembly of a relay means.

13 Claims, 7 Drawing Sheets

ULTRASOUND PROBE FOR ULTRASOUND EXAMINATION SYSTEM

BACKGROUND OF THE INVENTION

1. Field of the Art

This invention relates to an ultrasound examination system, and more particularly to an ultrasound probe which can be introduced into a body cavity through a narrow guide passage like a biopsy channel of an endoscope or the like.

2. Prior Art

Ultrasound probes of the sort which are adapted to be inserted into a body cavity by way of an endoscope or a similar guide means have been well known in the art and widely used for ultrasound examination systems. For instance, Laid-Open Japanese Patent Application H11-56836 discloses an ultrasound examination system employing an ultrasound probe which is designed to be introduced into a body cavity through a biopsy channel of an endoscope. The ultrasound probe of this ultrasound examination system has an ultrasound scanner head with an ultrasound transducer element, attached to the fore distal end of a flexible cord to be inserted into an endoscopic biopsy channel. A connector is provided at the base or proximal end of the flexible cord for connection to an ultrasound image observation terminal with an ultrasound signal processor and a viewing screen.

In a case where an endoscopic biopsy channel is used as a guide means, as a matter of course the outside diameter of the ultrasound probe depends on the inside diameter of the endoscopic biopsy channel. In this regard, it is the flexible cord of the probe that is placed within a biopsy channel of an endoscope. The ultrasound probe may be introduced into an endoscopic biopsy channel either through an entrance opening of the biopsy channel through which a biopsy or surgical instrument is normally inserted into the biopsy channel or inversely through an exit opening through which an inserted biopsy or surgical instrument is projected within a body cavity. This means that at least one end of the ultrasound probe is free from diametrical restrictions as imposed by the inside diameter of the biopsy channel. Namely, the diameter of the ultrasound scanner head at the fore distal end of the flexible cord or of the connector at the proximal end f the flexible cord can be larger than that of the endoscopic biopsy channel. In the case of the prior art ultrasound probe mentioned above, the ultrasound scanner head which accommodates a large-size ultrasound transducer element is larger than the endoscopic biopsy channel in diameter, while the flexible cord and connector are formed smaller than the inside diameter of the biopsy channel. Because of fragility of the thin and narrow connector, an adaptor is detachably attached to the connector at the time of coupling same with an ultrasound scan control unit which is connected from an ultrasound image observation terminal.

In this instance, the ultrasound transducer which is provided on the above-mentioned prior art ultrasound probe is of a single-element type which is adapted for mechanical radial scans. For this purpose, threaded through the flexible cord is a flexible transmission shaft having tightly wound coils fitted within a flexible sleeve to transmit rotations to the ultrasound transducer element, which is connected to the fore distal end of the flexible shaft. The opposite base end of the flexible shaft is coupled with a rotational shaft which is provided within the connector. The rotational shaft of the connector is connected to a drive shaft which is provided within a casing of the ultrasound scan control unit, along with an electric drive motor which is coupled with the drive shaft and an encoder which is provided in association with the drive shaft to detect rotational angles of the latter.

In addition to the ultrasound probes of the above-mentioned mechanical radial scan type, there have been in use the so-called electronic scan type ultrasound probes. In the case of an electronic scan type probe, the ultrasound transducer consists of a large number of transducer elements which are arranged in a predetermined direction, for example, in a linear direction or in radial directions. A signal cable is connected to each one of the ultrasound transducer elements to transmit and receive ultrasound signals separately by the respective transducer elements. In the case of an electronic scan type ultrasound probe of this sort, the pattern or focus position of an ultrasound scan can be changed to cope with various ultrasound examinations, by suitably adjusting the drive timing of the respective ultrasound transducer elements.

Since the ultrasound transducer on an electronic scan type probe contains a large number of transducer elements, it is difficult to reduce its diameter down to a size which can easily pass through a biopsy channel of an endoscope. However, as in the case of the above-mentioned prior art probe construction, the ultrasound probe can be placed in an endoscopic biopsy channel by inserting the probe through an exit opening of the biopsy channel at the fore distal end of the endoscope. For an electronic scan type ultrasound probe, it is not necessary to have a flexible transmission shaft within the flexible cord which is connected to the ultrasound scanner head. Therefore, a necessary number of signal cables can be relatively easily passed through the flexible cord if the diameter of each signal cable is reduced to a suitable degree. However, in the case of an electronic scan type ultrasound probe which requires a large number of contact points, it becomes necessary to provide a large connector at the proximal end of the flexible cord. In short, in the case of an electronic scan type probe, larger the number of the ultrasound transducer elements, larger becomes the size of the connector. Therefore, even if the flexible cord of an electronic scan type probe is thin and narrow enough for passage through an endoscopic biopsy channel, it has been often found difficult to insert the probe into a narrow guide channel or passage of an endoscope because of bulkiness of the ultrasound scanner head and the connector which are provided at the head and tail ends of the flexible cord, despite various advantages of electronic scan type probe in ultrasound examinations.

SUMMARY OF THE INVENTION

Under the circumstances as discussed above, it is an object of the present invention to make it possible to insert and place an electronic scan type ultrasound probe into a narrow passage like a biopsy channel of an endoscope.

It is another object of the present invention to make it possible to insert into and pass through a narrow guide passage a connector portion which is provided at the proximal end of a flexible cord of an electronic scan type ultrasound probe and which usually incorporates a large number of terminals for connection to an ultrasound signal processor of an ultrasound image observation terminal.

In order to achieve the above-stated objectives, according to the present invention, there is provided an ultrasound probe for use on an ultrasound examination system which is largely composed of an ultrasound probe to be introduced into a body cavity by way of a guide passage and an ultrasound image observation terminal, the ultrasound probe including an ultrasound scanner head attached to a distal end of a flexible cord to be placed in the guide passage at the time of introduction into a body cavity and constituted by a plural number of ultrasound transducer elements for making electronic scans, a plural number of signal lines passed through the flexible cord and connected respectively to the ultrasound transducer elements, a proximal end portion of the flexible cord being led out of the guide passage and disconnectibly connected to an ultrasound signal processor of the ultrasound image observation terminal, characterized by the provision of: a flexible wiring film in the shape of a relatively narrow strip having a root end portion thereof fixedly attached to a proximal end portion of the flexible cord of the ultrasound probe and adapted to be coiled into a helical roll of a cylindrical shape along an axial extension line of the flexible cord for passage through the guide passage; the flexible wiring film having a plural number of wire connection points formed on a surface thereof at positions closer to the root end for connection thereto of the signal lines from the ultrasound transducer elements, and a plural number of electrodes formed in intermediate and opposite end portions and each connected with a corresponding one of the wire connection points through a wiring pattern; the electrodes of the flexible wiring film being adapted to be disconnectively connected to contact points provided on a contact unit of a relay means.

An ultrasound probe is introduced into a body cavity to transmit and receive ultrasound signals through an intracavitary wall. However, the ultrasound is not introduced into a body cavity by itself. It is usually inserted through a guide passage, typical of which is a biopsy channel which is provided on an endoscope. Besides the biopsy channel, other guide means can be used for introduction of the ultrasound probe. Regarding the ultrasound transducer, the respective transducer elements may be arrayed circularly, arcuately or linearly depending upon the mode of electronic scans.

The flexible wiring film, a wiring board in the form of a flexible film, is attached to a proximal end portion of the flexible cord of the ultrasound probe. In this regard, the flexible wiring film can be formed integrally with a sheathing tube of the flexible cord. However, from the standpoint of efficiency of fabrication process, it is desirable to form the flexible cord and the flexible wiring film separately, fixing the flexible wiring film on the sheathing tube of the flexible cord afterwards. The flexible wiring film may be bonded on a circumferential surface of the sheathing tube of the flexible cord. However, in order to facilitate connections of signal lines from the flexible cord, it is more desirable to provide an longitudinal slot-like opening of a suitable length in a proximal end portion of the sheathing tube and to securely fix the root end portion of the flexible wiring film within the slot-like opening.

The wire connection points are formed in a row or rows and at positions in the proximity of the slot-like opening in the sheathing tube of the flexible cord. The signal lines that are led out of the flexible cord are connected to the wire connection point by soldering. These wire connection points, wiring pattern and electrodes can be formed on the flexible wiring film, for example, by the use of a printing means. For connection of the signal lines, each one of the wire connection points suffices to have a small surface area. Accordingly, the wire connection points can be located collectively on a root end portion of the flexible wiring film. On the other hand, the electrodes to be brought into and out of engagement with the contact points on the side of the contact assembly of the relay means need to have a broader surface area as compared with the wire connection points. Accordingly, the electrodes having a broader surface area are located dispersedly in intermediate and opposite outer end portions of the flexible wiring film. Thus, the width and length of the flexible wiring film are determined mainly in relation with the size and number of the electrodes. Especially, the length of the flexible wiring film can be increased to a sufficient degree, if necessary, because the film is coiled into the shape of a partially overlapped helical roll at the time of passage through a guide passage.

When coiled into the shape of a helical roll, the flexible wiring film should be easily passable through a narrow guide passage. For this purpose, the flexible wiring film is rolled into a cylindrical shape gradually from the root end portion which is connected to the flexible cord of the probe. In the case of a flexible wiring film with a broader surface area, in order to hold the flexible wiring film stably in the coiled shape, that is, in the cylindrical shape, it is desirable to extend the flexible wiring film obliquely in the rearward direction relative to the longitudinal axis of the flexible cord of the probe. By so doing, the flexible wiring film strip can be easily coiled into a partially overlapped helical roll. To prevent uncoiling or unrolling of the rolled flexible wiring film, it is necessary to stop the free end of the film. For this purpose, a rubber band or an adhesive tape can be used. Alternatively, a flexible sheath member may be fitting on the free end of the film. Further, the flexible wiring film may be imparted with a convolving traits beforehand in order to facilitate the job of coiling same into a partially overlapped helical roll.

For connection to contact points, the flexible wiring film needs to be set in a flat state on the contact unit. For this purpose, the contact unit is constituted by a contact assembly and a pressing member. A predetermined number of contact points are provided on a top surface of the contact assembly correspondingly to the electrodes on the side of the flexible wiring film which is set on the top surface, and the pressing member is closed on the contact assembly, pressing the interposed flexible wiring film against the contact assembly to electrically connect the electrodes to the corresponding contact points on the contact assembly. Alternatively, arrangements may be made to fix the flexible wiring film on the contact assembly by the use an adhesive or other means. One side of the pressing member can be flexibly connected to one side of the contact assembly by the use of a hinge or hinges. In this case, for locking the pressing member in a closed pressing position on the contact assembly, it is desirable to provide a lock means between these members.

Preferably, a resilient pad member, for example, is provided on an inner surface of the pressing member thereby to electrically connect the electrodes of the flexible wiring film with the contact points on the contact assembly securely in a reliable manner. Further, for positioning the electrodes of the flexible wiring film correctly relative to the contact points on the contact assembly, it is desirable to provide a plural number of positioning projections on the top surface of the contact assembly for engagement with positioning perforations which are provided on the side of the flexible wiring film. Of course, the electrodes on the flexible wiring film can be brought into position relative to the contact points on the contact assembly in reference to the shape of the flexible wiring film and a marking which is provided on the top surface of the contact assembly. Further, preferably, the contact assembly is constituted by contact pins which are retractably projected on the top surface of the contact assembly and spring member which are adapted to bias the contact pins in a projecting direction.

The above and other objects, features and advantages of the present invention will become apparent from the following particular description of the invention, taken in conjunction with the accompanying drawings. Needless to say, the present invention should not be construed as being limited to particular forms shown in the drawings which show by way of some preferred embodiments of the invention.

DESCRIPTION OF PREFERRED EMBODIMENTS

Figure 1:
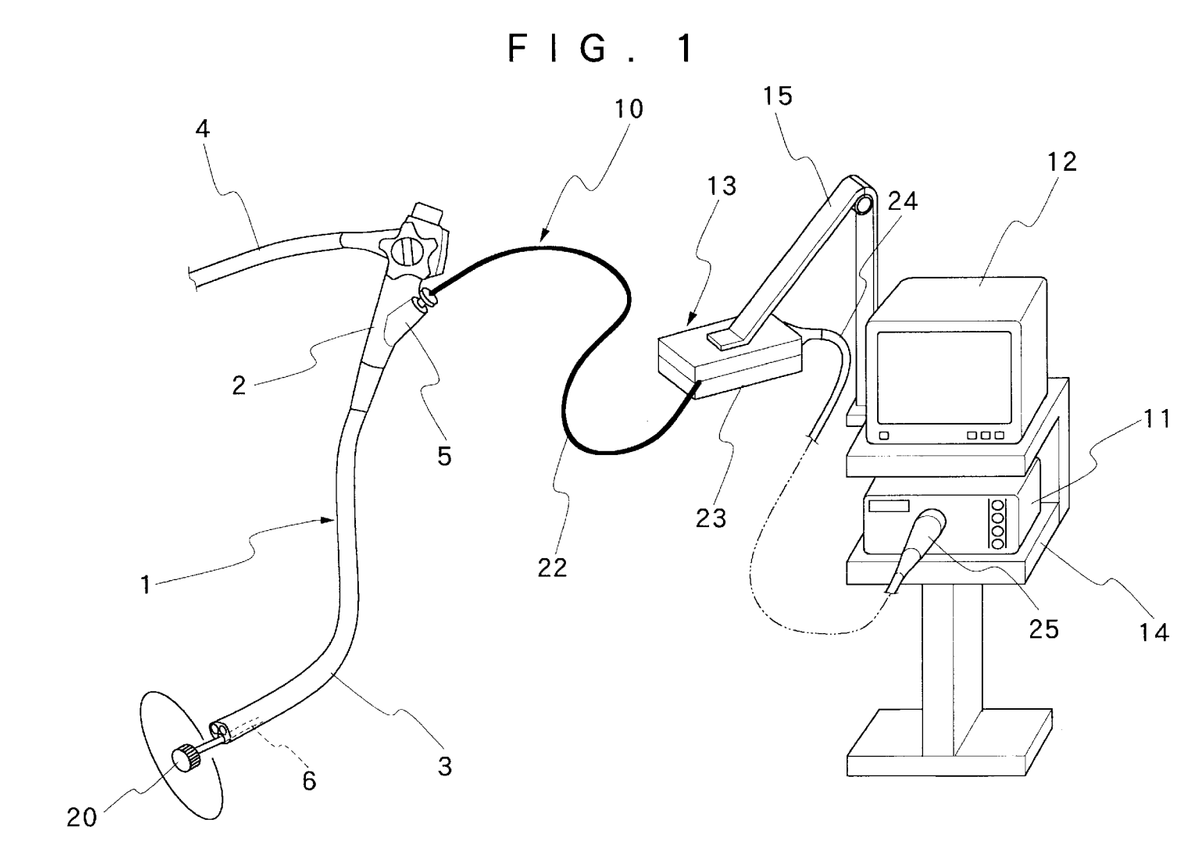
FIG. 1 is a schematic illustration of general layout of an ultrasound examination system embodying the present invention, showing together an endoscope which is employed as a guide means.

Hereafter, the present invention is described more particularly by way of preferred embodiments with reference to the accompanying drawings. Referring first to FIG. 1, there is shown general configuration of an ultrasound examination system. In the case of this embodiment, the ultrasound examination system employs by way of example an ultrasound probe which is adapted to be introduced into a body cavity of a patient by way of a biopsy channel of an endoscope or a similar guide means.

In that figure, indicated at 1 is an endoscope which has an insertion instrument 3 extended out from a manipulating head assembly 2 for insertion into a body cavity. A universal cable 4 which is led out from the opposite side of the manipulating head assembly 2 is for connection to a light source (or an image processor). An entrance housing 5 is provided on the manipulating head assembly 2 for insertion of biopsy or surgical instruments such as forceps, a high frequency tool and so forth. Although not shown in the drawings, the entrance housing 5 leads to a biopsy channel 6 which is formed coextensively within the insertion instrument 3 toward an exit opening which is provided in an end face at the fore distal end of the insertion instrument 3.

Denoted at 10 is an ultrasound probe, at 11 an ultrasound image processor, at 12 a viewing screen for monitoring ultrasound images, and at 13 a relay means. Provided at the fore distal end of the ultrasound probe 10 is an ultrasound scanner portion accommodating an ultrasound transducer 20 to make electronic ultrasound scans. The relay means 13 includes a contactor unit 23, and a connecting cable 24 which is led out from the contactor unit 23 and provided with a connector 25 at its distal end. The connector 25 of the connecting cable 24 is disconnectibly connectible to the ultrasound image processor 11. The contactor unit 23 is supported on a flexible arm 15 which is in turn supported on a rack 14 of the ultrasound image processor 11.

Figure 2:
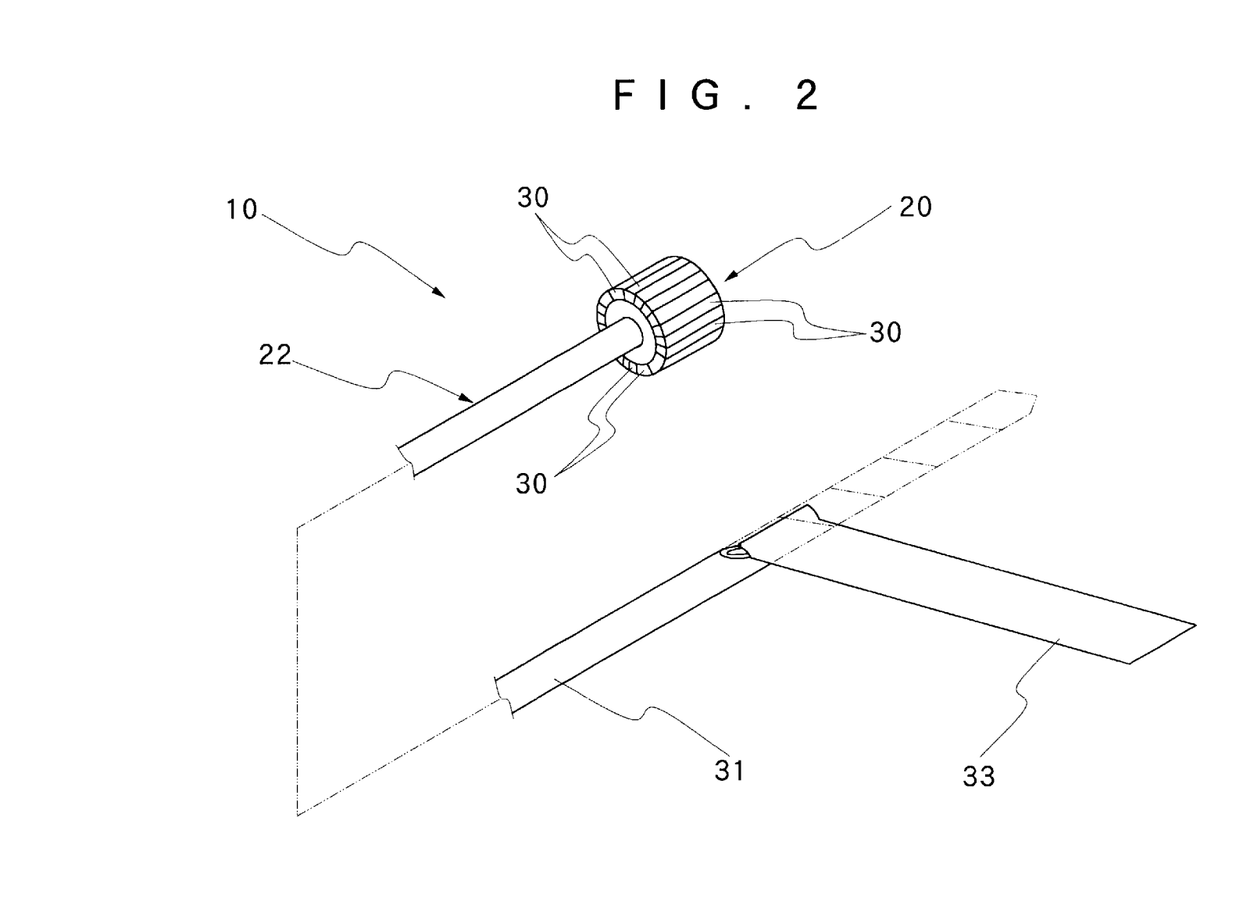
FIG. 2 is a schematic view of an ultrasound probe.

Shown in FIG. 2 is the general layout of the ultrasound probe 10. As clear therefrom, the ultrasound transducer 20 is cylindrical in shape and has a large number of transducer elements 30 arranged circularly around its circumference. These circularly arranged transducer elements 30 are driven sequentially at the time of a radial electronic scan. In this instance, a radial ultrasound scan can be made by driving the transducer elements 30 of the ultrasound transducer 20 sequentially one after another. Alternatively, an ultrasound scan of an arbitrary ultrasound signal transmission pattern can be made by dividing the transducer elements 30 into a number of groups and simultaneously or sequentially driving transducer elements 30 of a selected group.

Figure 3:
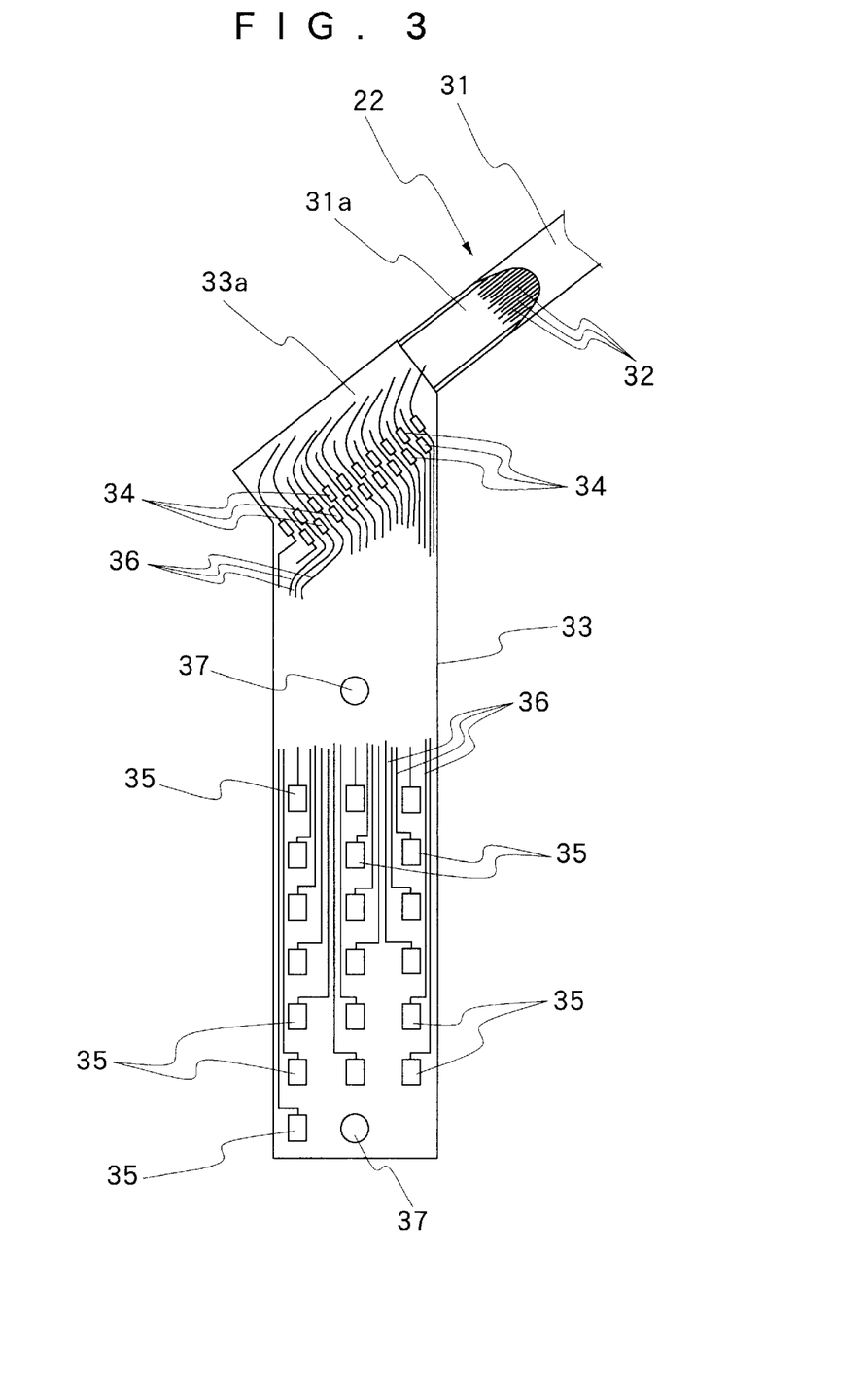
FIG. 3 is a schematic view of a flexible wiring film in a flatly stretched state.

The ultrasound transducer 21 is connected to the fore end of the flexible cord 22 which contains, within a flexible sheathing tube 31 of a synthetic resin material, a large number of signal lines 32 to or from the respective transducer elements 30 of the transducer 20. As shown in FIG. 3, the sheathing tube 31 is provided with a longitudinal slot-like opening 31a which is formed by cutting off part of a proximal end portion of the sheathing tube 31 over a predetermined axial length, and a flexible wiring film 33 is attached to the slot-like opening 31a. More specifically, the flexible wiring film 33 is in the shape of a relatively narrow strip which is extended obliquely in the rearward direction relative to the longitudinal axis of the flexible cord 22, the flexible wiring film 33 having a root end portion 33a to be bonded to the slot-like opening 31a for connection thereto.

Formed on a front surface of the flexible wiring film 33 are a plural number of wire connection points 34 and electrodes 35, in one on one relation with the signal lines 32, and a wiring pattern 36 which connects the wire connection points 34 with corresponding electrodes 35. These wire connection points 34, electrodes 35 and wiring pattern 36 can be formed on the flexible wiring film 33 by printing or by other means known in the art. The wire connection points 34 are arranged in a row or rows (in two rows in the case of the particular embodiment shown) on the root end portion 33a of the flexible wiring film 33, and corresponding signal wires 32 are connected to the respective wire connection points 34 by soldering, bonding or other suitable means. On the other hand, the electrodes 35 are dispersedly located over a broad area on a fore end portion of the flexible wiring film 33. In comparison with the wire connection points 34, the electrodes 35 have a broader surface area. This is because is suffices for the wire connection points 34 to have a relatively small surface area for wiring the signal lines 32 but the electrodes 35 need to have a broader surface area to establish secure and stable connection with contact points 46 of the contactor unit 23 of the relay means 13, which will be described hereinlater. Further, the flexible wiring film 33 is provided with at least two positioning perforation 37, one in its intermediate portion and the other one in its fore end portion.

In this instance, the outside diameter of the ultrasound probe 10, which is to be introduced into a body cavity by way of the biopsy channel 6 of the endoscope 1, depends on the inside diameter of the biopsy channel 6. Namely, the ultrasound probe 10 cannot be inserted into the endoscopic biopsy channel 6 if its outside diameter is larger than the inside diameter of the biopsy channel 6. However, as clear from FIG. 1, it is only the flexible cord 22 that is placed within the endoscopic biopsy channel 6. Therefore, the flexible cord 22 should be thinner in diameter than the biopsy channel 6. In this regard, the flexible cord 22, which has the signal cables 32 encased in the flexible sheathing tube 31 as explained hereinbefore, can be downsized to a smaller diameter as compared with the biopsy channel, by adjusting the diameter of the signal wires 32 and the thickness of the sheathing tube 31. In contrast, the ultrasound transducer 20, with a large number of transducer elements 30 for electronic scanning operation, is thicker in diameter than the endoscopic biopsy channel, and therefore cannot be passed through the latter. However, there is no necessity for passing the ultrasound transducer 20 through the endoscopic biopsy channel 6 in a case where the ultrasound probe 10 is introduced into the biopsy channel 6 inversely through the opening at the fore end of the biopsy channel 6.

Figure 4:
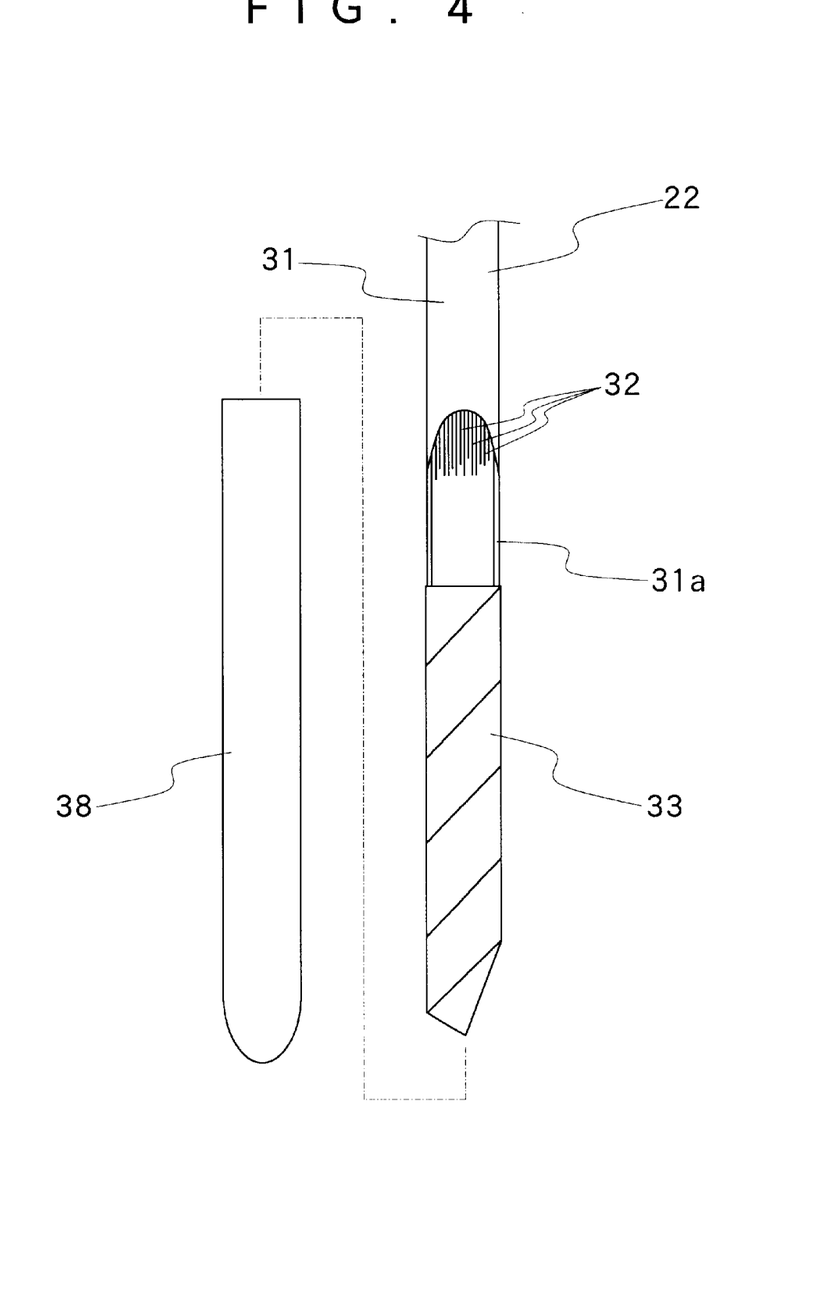
FIG. 4 is a schematic view of the flexible wiring film, shown in a helically rolled state along with a sheath member.

In this connection, the flexible wiring film 33 which is stemmed out from a base end portion of the ultrasound probe 10 has to be passed through the endoscopic biopsy channel 6. The flexible wiring film 33 is formed of a narrow stip of a flexible film and extended obliquely in a rearward direction relative to the longitudinal axis of the flexible cord 22. The strip of the flexible wiring film 33 is formed into a helical roll, that is, helically rolled into a cylindrical shape along an extension line of the flexible cord 22 as indicated by an imaginary line in FIG. 2 or as indicated by a solid line in FIG. 4. In order to prevent unrolling, the free end of the helically rolled flexible wiring film 33 is placed in a tubular flexible sheath member 38. In helically rolling the flexible wiring film 33 into a cylindrical shape, it should be tightly convolved to have an outside diameter which is substantially same as that of the flexible cord 22. In such a state, the rear end of the ultrasound probe 10 can be passed through the endoscopic biopsy channel, from the exit opening at the fore distal end of the insertion instrument 3 of the endoscope 1.

The capped sheath member 38 is removed after withdrawing the rolled flexible wiring film 33 to the outside through the entrance housing 55 on the manipulating head assembly of the endoscope 1. Now, the flexible wiring film 33 can be unrolled into a flat sate. The respective electrodes 35 on the flexible wiring film 33 are then electrically connected to the ultrasound image observation terminal 11 through the relay means 13 thereby to permit transmission and reception of signals to and from to and from the respective transducer elements of the ultrasound transducer 20. The construction of contactor unit 23 of the relay means 13 is described more particularly below with reference to FIGS. 5 to 8.

Figure 5:
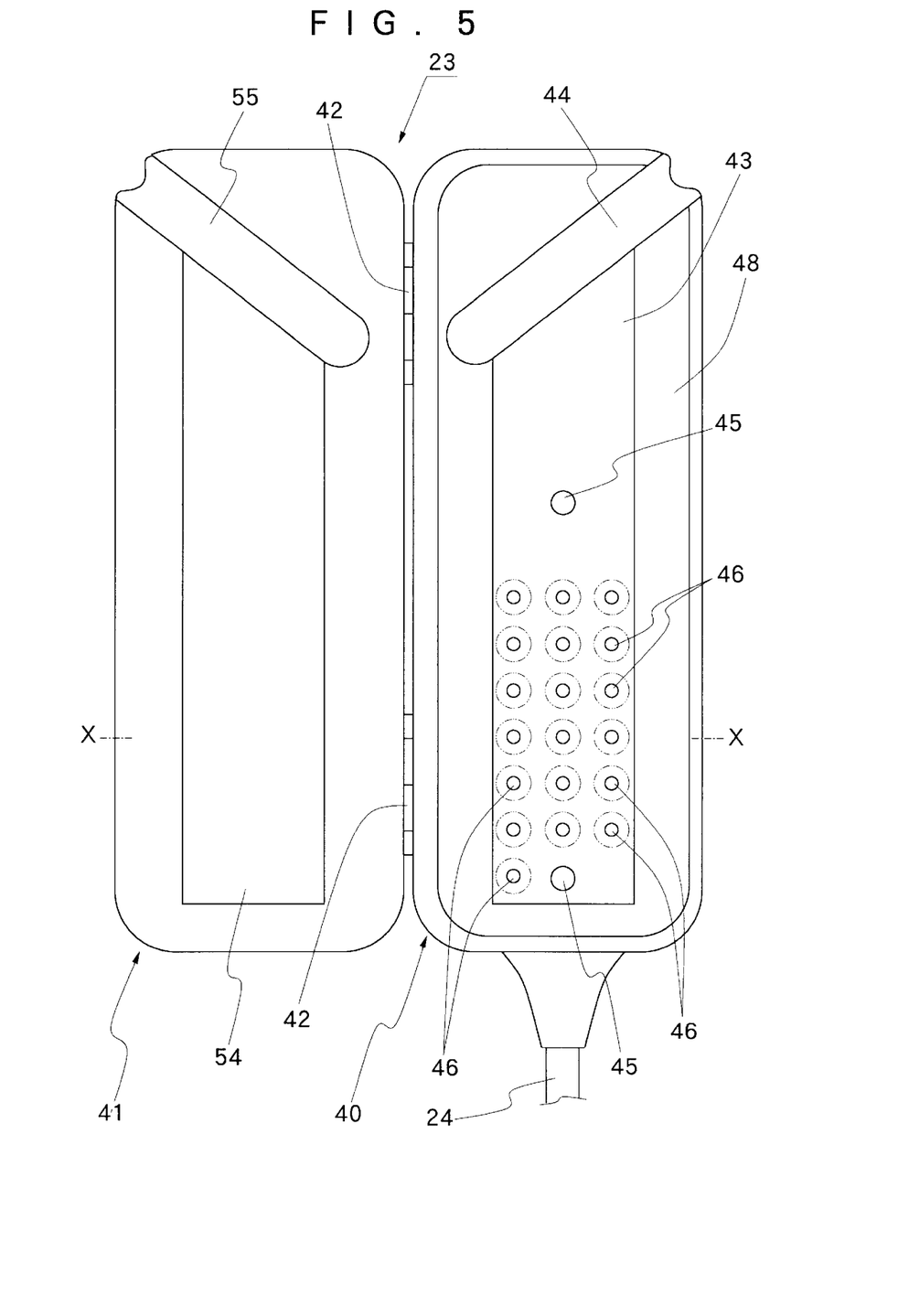
FIG. 5 is a schematic plan view of a contactor unit of a relay means, showing contact members and pressing members in an opened state.
Figure 6:
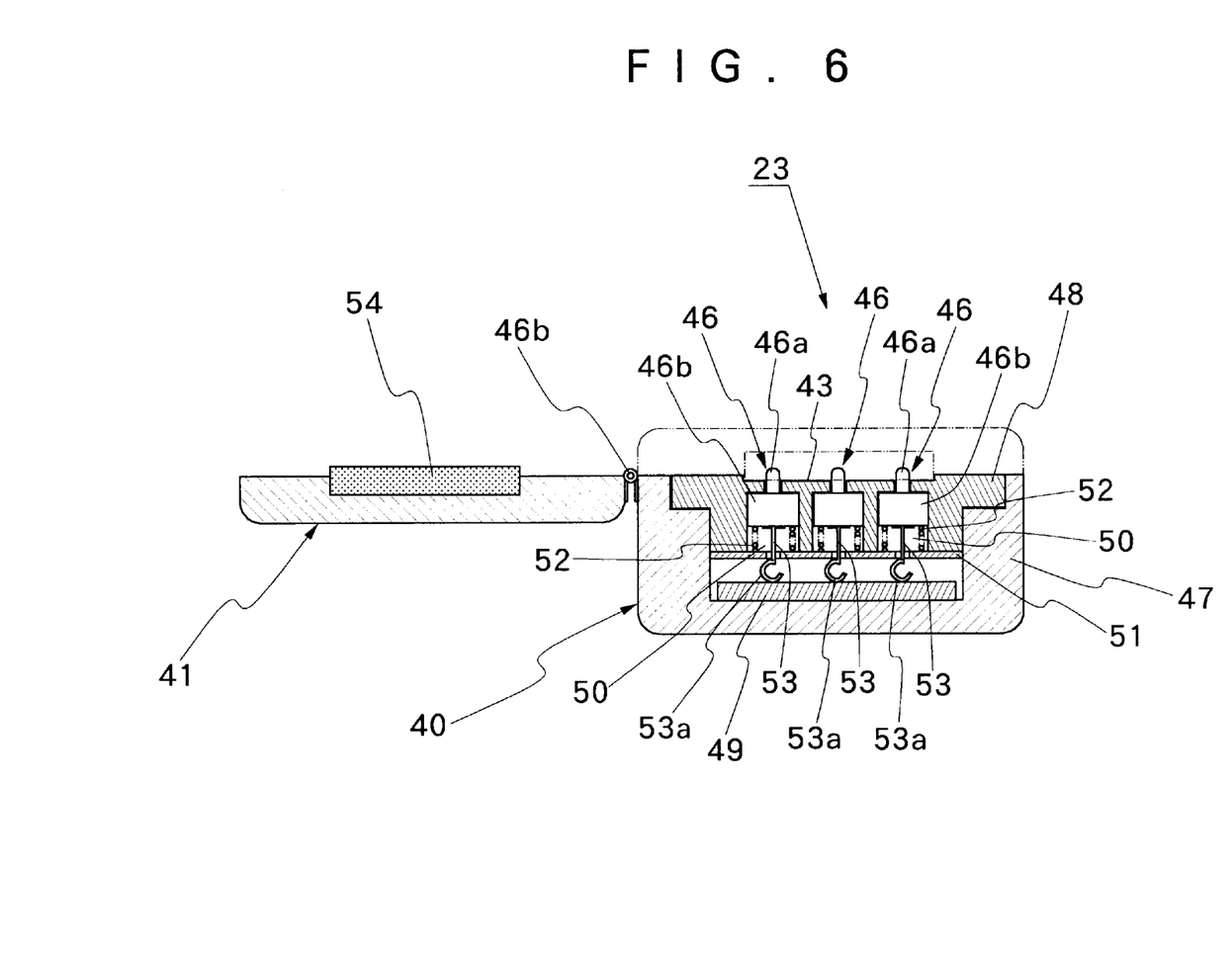
FIG. 6 is a schematic sectional view of the contactor unit, taken on line X—X in FIG. 5.

As shown particularly in FIGS. 5 and 6, the contactor unit 23 is composed of a contact assembly 40 and a pressing member 41. The pressing member is pivotally connected to the contact assembly 40 by means of hinges 42 and swingable toward and away from the latter between an open position indicated by a solid line in FIG. 6 and a closed position indicated by an imaginary line in the same figure. Formed on a top surface of the contact assembly 40, which meets the pressing member 41, are a wiring film mount portion 43 and a cord receptacle groove 44 to receive therein a fore end portion of the flexible cord 22 and the flexible wiring film 33, respectively. The flexible wiring film 33 which is unrolled into a flat shape is placed on the wiring film mount portion 43, with the electrodes 35 in abutting engagement with the latter. Since the flexible wiring film 33 is put in a helically rolled shape at the time of insertion into the endoscopic biopsy channel 6, it is desirable that the flexible wiring film 33 be curled or imparted with a convolving trait beforehand for the purpose of facilitating the job of rolling same. Therefore, positioning projections 45 are provided on the wiring film mount portion 43, at two separate positions. These positioning projections 45 are engaged with positioning perforations 37 on the side of the flexible wiring film 33 upon setting the latter on the wiring film mount portion 43. In this regard, desirably the positioning projections are arranged to snap into the positioning perforations, for holding the flexible wiring film 33 stably in position on the wiring film mount portion 43. Accordingly, by the positioning projections 45, the flexible wiring film 33 is fixed correctly in position on the wiring film mount portion 43 in a flatly stretched state even in a case where the film is curled or imparted with a convolving trait.

Figure 7:
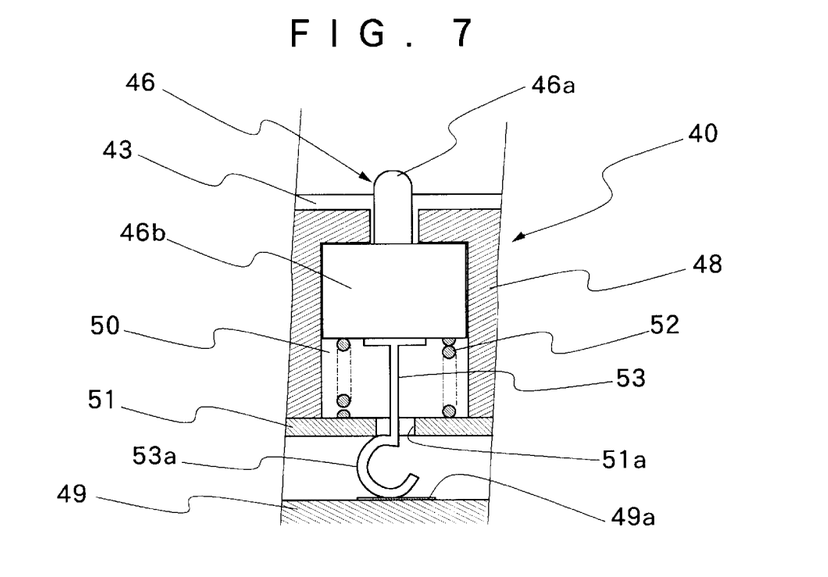
FIG. 7 is an enlarged schematic sectional view of a contactor unit.
Figure 8:
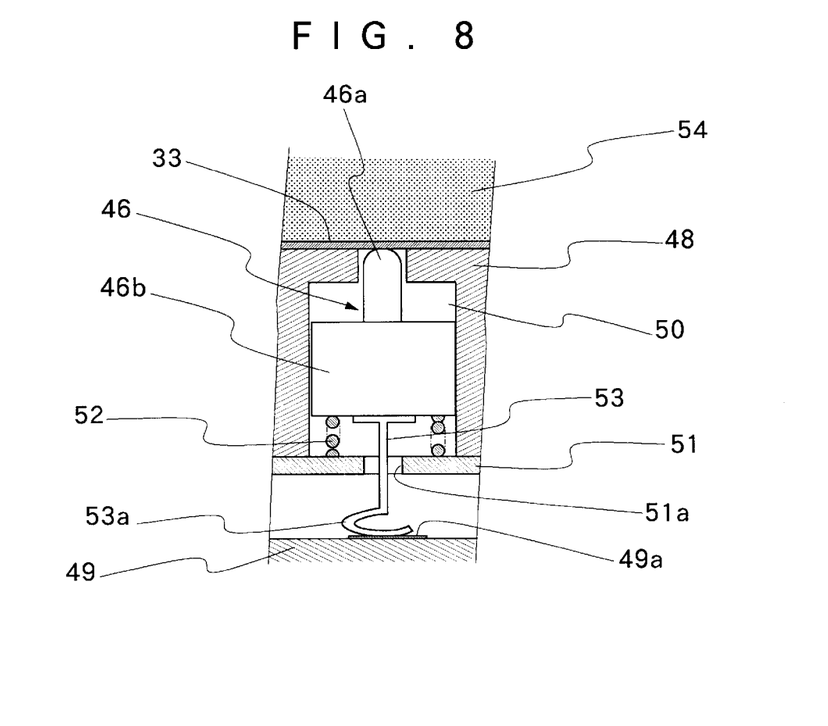
FIG. 8 is a view similar to FIG. 7 but showing the contactor unit in a different operational phase.

The wiring film mount portion 43 of the contact assembly 40 is provided with a plural number of contact points 46 correspondingly in position and number to the electrodes 35 on the side of the flexible wiring film 33 which is set on the wiring film mount portion 43. As shown in FIGS. 7 and 8, each one of the contact points 46 is constituted by a contact pin member 46a which is spherically rounded at its head end and provided with a flange portion 46b at its tail end. In this instance, the contact assembly 40 is largely constituted by a base member 47, a contact block 48 which is fitted in the base member 47 and securely fixed to the latter by screws or other suitable means, and a relay wiring board 49 which is placed in a space which is formed between the base member 47 and the contact block 48. Provided in the contact block 48 are rows of compartments 50 for receiving the respective contact pins 46. A bottom plate 51 is attached to the bottom side of the contact block 48.

The wiring film mount portion 43 is defined by a sunken surface which is provided on the top side of the contact block 48. Each one of the compartments is provided with a hole which is opened to the top side of the contact block 48 within boundaries of the wiring film mount portion 43. The contact pin 46a in each compartment 50 is retractably protruded on the top side of the contact block 48 through the just-mentioned hole. Interposed between the flange portion 46b of each contact pin 46a and the bottom plate 51 is a spring 52 thereby to urge the rounded head of the contact pin 46a to protrude on the top side of the contact block 48 by a predetermined length. Further, securely fixed to the bottom side of the flange portion 46b of each contact pin 46a is one end of a contact spring member 53, which is extended downward through a hole 51a, which is provided in the bottom plate 51, and provided with a hook-like contact portion 53a of substantially C-shape at the other lower end. As shown in FIG. 7, this contact portion 53a is held in contact with one of electrodes 49a which are formed on the relay wiring board 49. Therefore, as the contact point 46 which is projected on the top surface of the contact block 48 is pressed inward against the biasing force of the spring 52, the contact spring member 53 which is fixedly connected with the contact pin 46a is resiliently deformed into a flattened shape and pressed against the electrode 49a on the side of the relay wiring board 49.

The pressing member 41 which is pivotally connected to the contact assembly 40 through the hinges 42 is provided with a resilient pad 54 on its inner surface to be closed on the contact assembly 40, opposingly to the flexible wiring film mount portion 43 on the top side of the side of the contact assembly 40 for pressing the flexible wiring film 33 against the wiring film mount portion 43. The resilient pad 54 has a predetermined thickness, and is projected from the inner surface of the pressing member 41 by its thickness. Accordingly, as the pressing member 41 is closed on the contact assembly 40 through the interposed flexible wiring film 33, the flexible wiring film 33 is pressed against the contact points 46 by the resilient pad 54, pushing in the contact points 46 against the biasing force of the springs 52 in the manner as shown in FIG. 8. Although not shown in the drawings, lock means is provided between the contact assembly 40 and the pressing member 41 to retain or lock the latter in the closed position. Such lock means can be easily realized by the use of conventional lock means.

As a consequence, all of the electrodes 35 on the flexible wiring film 33 are securely held in abutting engagement with the corresponding contact points 46, and the contact spring members 53 which are connected with the contact points 46 are pressed against the corresponding electrodes 49a on the relay wiring board 49. That is to say, all of the electrodes 35 on the flexible wiring film 33 are electrically connected with the corresponding electrodes 49a on the relay wiring board 49. The relay wiring board 49 is connected with signal lines of the connecting cable 24. Therefore, upon plugging the connector 25 at the proximal end of the connecting cable 24 to the ultrasound image observation terminal 11, the signal lines to or from the respective transducer elements 30 of the ultrasound transducer 20 are connected to a signal transmission/reception circuit of the ultrasound image observation terminal 11.

In addition and similarly to the contact assembly 40, a cord receptacle groove 55 is provided also on the pressing member 41. The contact unit 23, which is constituted by the assembly 40 and the pressing member 41, is arranged to grip therebetween a proximal end portion of the flexible cord 22 along with the flexible wiring film 33. Therefore, even if the flexible wiring film 33 is reduced in thickness, there is little possibility of rupturing of the flexible wiring film or detachment of its bonded root end portion from the sheathing tube 31 of the flexible cord 22.

The above arrangements make it possible to insert into a body cavity the ultrasound transducer 20 which employs a large number of transducer elements 30 in an array for electronic ultrasound scans, by way of a narrow guide passage like the biopsy channel 6 of the endoscope 1. In a case where there is a need for increasing the number of ultrasound transducer elements 30 to meed a demand for higher resolution of ultrasound images, this can be coped with simply by increasing the surface area of the flexible wiring film 33. For example, the surface area of the flexible wiring film 33 can be increased by increasing its size in the longitudinal direction. In such a case, the size of the flexible wiring film 33 remains unchanged except for its length, more specifically, except that its length is increased when it is helically rolled into a cylindrical shape. Besides, the flexible wiring film 33 still has a suitable degree of flexibility in bending directions. Therefore, the flexible wiring film 33 can be smoothly passed through the endoscopic biopsy channel 6 along with the flexible cord 22, and all of the ultrasound transducer elements 30 can be connected to the ultrasound image observation terminal in a secure and reliable manner.

What is claimed is:

1. An ultrasound probe to be introduced into a body cavity by way of a guide passage and an ultrasound image observation terminal with an ultrasound signal processor and a viewing screen, said ultrasound probe including an ultrasound scanner head attached to a distal end of a flexible cord to be placed in the guide passage at the time of introduction into a body cavity and constituted by a plural number of ultrasound transducer elements for making electronic scans, a plural number of signal lines passed through said flexible cord and connected respectively to said ultrasound transducer elements, a proximal end portion of said flexible cord being led out of said guide passage and disconnectibly connected to said ultrasound image observation terminal; said ultrasound probe comprising:
a flexible wiring film in the shape of said relatively narrow strip having a root end portion thereof fixedly attached to said proximal end portion of said flexible cord of said ultrasound probe and adapted to be coiled into a helical roll substantially of a cylindrical shape along an axial extension line of said flexible cord for passage through said guide passage;
said flexible wiring film having a plural number of wire connection points formed on a surface thereof at positions closer to said root end for connection thereto of said signal lines from said ultrasound transducer elements, and a plural number of electrodes formed in intermediate and opposite end portions and each connected with a corresponding one of said wire connection points through a wiring pattern; and
said electrodes of said flexible wiring film being adapted to be disconnectively connected to contact points provided on a contact unit of a relay means.

2. An ultrasound probe as defined in claim 1, further comprising a slot-like opening provided in a rear end portion of a sheathing tube of said flexible cord, said root end of said flexible wiring film being securely fixed to said sheathing tube of said flexible cord across said slot-like opening, said wire connection points being located in a row or rows in the vicinity of said slot-like opening, and said signal lines from said ultrasound transducer elements being led out of said sheathing tube of said flexible cord through said slot-like opening and connected to said wire connection points on said flexible wiring film.

3. An ultrasound probe as defined in claim 1, wherein said wire connection points, wiring pattern and electrodes are formed on said flexible wiring film by printing, and said electrodes have a broader surface area than said wire connection points.

4. An ultrasound probe as defined in claim 1, wherein said flexible wiring film is in the form of a relatively narrow strip and attached to said flexible cord angularly to extend in an obliquely rearward direction relative to longitudinal axis of the latter, said flexible wiring film being adapted to be coiled into a helical roll of a cylindrical shape at the time of passage through said guide passage.

5. An ultrasound probe as defined in claim 4, wherein said flexible wiring film is retained in the form of a helical roll by fitting thereon a flexible tubular sheath member.

6. An ultrasound probe as defined in claim 4, wherein said flexible wiring film is imparted with a convolving trait beforehand and readily transformable into the shape of a helical roll.

7. An ultrasound probe as defined in claim 1, wherein said flexible wiring film is in the form of a relative narrow strip extended axially along an extension line of said flexible cord and retained in the shape of a helical roll by tucking in a free end thereof.

8. An ultrasound probe as defined in claim 1, wherein said contact unit is composed of a contact assembly and a pressing member adapted to grip therebetween said flexible wiring film in a flat state, said contact assembly being provided with a plural number of contact points on a top surface for connection with corresponding electrodes on the side of said flexible wiring film, and said pressing member being adapted to press said flexible wiring film against said contact assembly.

9. An ultrasound probe as defined in claim 8, wherein said pressing member is hinged to said contact assembly and closable on the latter at the time of connecting said electrodes of said flexible wiring film with said contact points on the side of said contact assembly.

10. An ultrasound probe as defined in claim 8, wherein said pressing member is provided with a resilient pad on an inner surface to be closed on said contact assembly and adapted to press said flexible wiring film against the latter through said resilient pad.

11. An ultrasound probe as defined in claim 8, wherein said contact assembly is provided with positioning projections at a number of separate positions on said top surface, said positioning projections being adapted to engage with perforations on the side of said flexible wiring film thereby to retain the latter in a predetermined position on said contact assembly.

12. Au ultrasound probe as defined in claim 8, wherein said contact points on said contact assembly are each arranged to have a spring action.

13. An ultrasound probe as defined in claim 1, wherein said guide passage is a biopsy channel of an endoscope.

* * * * *